United States Patent [19]  [11]  4,351,780
Giolito et al.  [45]  Sep. 28, 1982

[54] PROCESS FOR PREPARING ISOPROPYLPHENYL/PHENYL PHOSPHATE

[75] Inventors: Silvio L. Giolito, Whitestone, N.Y.; Stanley B. Mirviss, Stamford, Conn.

[73] Assignee: Stauffer Chemical Company, Westport, Conn.

[21] Appl. No.: 214,553

[22] Filed: Dec. 9, 1980

[51] Int. Cl.$^3$ .............................................. C07F 9/09
[52] U.S. Cl. .................................. 260/974; 260/976; 260/978; 260/980
[58] Field of Search ............... 260/973, 976, 978, 966, 260/974, 980; 568/756, 993

[56] References Cited

U.S. PATENT DOCUMENTS

Re. 29,540  2/1978  Randell et al. ...................... 260/966
3,859,395  1/1975  Terhune et al. ...................... 260/966

FOREIGN PATENT DOCUMENTS 1146173  3/1969  United Kingdom ................ 260/966

Primary Examiner—Anton H. Sutto
Attorney, Agent, or Firm—Roger S. Benjamin

[57] ABSTRACT

Monoisopropylphenyl/phenyl phosphate containing mixtures are prepared by, (1) alkylating phenol with propylene to $C_3/\phi$ ratio of less than 0.30 with a p-toluene sulfonic acid catalyst, (2) removing unreacted phenol as distillate to yield a distilland having a $C_3/\phi$ ratio above 0.3 and thereafter, (3) phosphorylating the distilland to yield a triaryl phosphate mixture having a reduced 2,6-diisopropylphenyl phosphate content.

5 Claims, No Drawings

PROCESS FOR PREPARING ISOPROPYLPHENYL/PHENYL PHOSPHATE

BACKGROUND OF THE INVENTION

Monoisopropylphenol or mixtures of monoisopropylphenol with phenol are useful feedstocks for phosphorylation to prepare isopropylated triaryl phosphates. These phosphate ester reaction products are high viscosity fluids having utility as hydraulic fluids and plasticizers.

Isopropylphenols are conventionally prepared by alkylating phenol with propylene in the presence of a Friedel-Crafts catalyst. The isopropylation of phenol yields a statistical distribution of products ranging from mono to di- and higher substituted phenols. Conventional procedures for preparing triaryl phosphates are described in U.S. Pat. Nos. Re. 29,540 and 4,139,487.

The presence of polyisopropyl phenols in phosphorylation feedstocks present several disadvantages. Sterically hindered polyisopropylphenols are more difficult to phosphorylate than monoisopropylphenol. In addition, certain phosphorylated products such as 2,6-diisopropylphenyl/phenyl phosphate are suspected of contributing to unwanted color formation in commercial isopropylphenyl/phenyl phosphate products.

The problem of eliminating unwanted polyisopropyl phenols has been dealt with by distillation of the alkylation reaction product prior to phosphorylation. Alternatively, unwanted polyisopropylphenyl/phenyl phosphates in the triaryl phosphate product have been removed by distillation under reduced pressure. Unfortunately, these prior art methods entail difficult fractionation procedures.

FIELD OF THE INVENTION

This invention relates to the preparation of isopropylphenyl/phenyl phosphates.

THE INVENTION

This invention is an improved process for preparing monoisopropylphenyl/phenyl phosphate mixtures by the phosphorylation of isopropylphenols. The isopropylphenyl/phenyl phosphate containing product has a reduced 2,6-diisopropylphenyl/phenyl phosphate content.

DETAILED DESCRIPTION OF THE INVENTION

The process of this invention prepares a monoisopropylphenyl/phenyl phosphate containing mixture by the sequential steps of (1) alkylation, (2) fractionation, and (3) phosphorylation.

Alkylation Step

It is a discovery of this invention that when phenol is alkylated with propylene under specific conditions the isopropylated phenol product is monoisopropylphenol having a reduced polyisopropylphenol, especially, a reduced 2,6-diisopropylphenol content. The polyisopropylphenol content in the monoisopropylphenol containing product mixture may be controlled in part by the alkylation step.

The degree of phenol isopropylation in the reaction product is designated the "$C_3/\phi$ ratio" and is defined as the ratio of the moles of propylene reacted with the total moles of phenol in the reaction system (including both isopropylated and non-isopropylated phenol).

The phenol alkylation is conducted by contacting phenol with propylene in a liquid reaction medium. Liquid phenol may constitute the reaction medium or the phenol may be dissolved or suspended in a nonreactive carrier or solvent. Suitable solvents include hydrocarbons, and halogenated hydrocarbons such as hexane, heptane, trichloroethylene, and perchloroethylene. Propylene may be introduced into the reaction zone as a gas or liquid. Gaseous propylene sparged into the reaction zone has the attendant advantage that it agitates the reaction medium.

A high level of agitation is important in conducting the alkylation step. In the absence of agitation localized concentrations of alkylated phenols build up in the reaction zone and encourage formation of polyisopropylated phenols. The level of agitation should be effective to substantially provide a uniform mixture of reactants in the reaction zone. Conventional agitation means such as impellers, static mixers, etc., are suitable for operation of the process.

The alkylation step of this invention employs a p-toluene sulfonic acid catalyst. The catalyst is used for liquid phase alkylation within a temperature range of 30° C. to 180° C. The alkylation may be done at atmospheric or superatmospheric pressure.

The concentration of p-toluene sulfonic acid catalyst is not critical and is typically used within the range of from about 0.5% to about 10% by weight of phenol in the alkylation reaction zone.

Time for performing the alkylation is not critical and will typically vary from about 1 hour to about 24 hours.

The course of alkylation may be monitored by determining the amount of propylene consumed by the reaction. Alternatively, samples of the reaction medium may be periodically withdrawn and analyzed by appropriate methods such as gas chromatography.

It has been discovered that the predominant product of the alkylation in the initial stages of the isopropylation reaction is monoisopropylphenol. As the reaction progresses the proportion of phenol in the reaction zone decreases and the likelihood of further isopropylating monoisopropylphenol increases. Thus, alkylating to high $C_3/\phi$ ratios encourages production of unwanted polyisopropylphenols. The $C_3/\phi$ ratio of the alkylation step of this invention should be less than 0.25 and preferably is in the range of 0.05 to 0.20.

The alkylation step reaction product contains phenol and monoisopropylphenol. The proportion of polyisopropylphenols is generally less than three weight percent of the reaction product. It has been found that the proportion of polyisopropylphenols in the alkylation product decreases with a decrease in the $C_3/\phi$ ratio. Therefore, it is possible to reduce polyisopropylphenol formation to any desired low level by varying the $C_3/\phi$ ratio from 0.3 downward.

Fractionation Step

The second essential process step is fractionation. This step has the purpose of preparing phenol/monoisopropylphenol mixtures having a monoisopropylphenol content high enough to make the mixture suitable for subsequent phosphorylation to yield triaryl phosphates of suitable viscosity.

Phenol has boiling point and vapor pressure characteristics which permit its facile separation from isopropylated phenols by distillative methods. The ease of the distillative separation of phenol from isopropylphenols is in contrast to the difficulty encountered in the fractionation of monoisopropylphenols from di- and higher- isopropylphenols. Moreover, the distillation temperatures required for the removal of phenol from a phenol/monoisopropylphenol mixtures are lower than those required for distillative separation of monoisopropylphenols from polyisopropylphenols. Lower distillation temperatures tend to minimize decomposition and other side effects.

The second step distillative fractionation of this invention separates unreacted phenols as distillate and prepares a product distilland having an enhanced monoisopropylphenol content. The distillation is carried out until a $C_3/\phi$ ratio of at least 0.30 in the distilland is obtained. Preferably, the $C_3/\phi$ ratio of the distilland is from 0.35 to 0.60. Thus, a feedstock from the alkylation step having a $C_3/\phi$ ratio of less than 0.30 (preferably 0.05 to 0.20) is distilled to give a distilland having a $C_3/\phi$ ratio of at least 0.30 (preferably 0.35 to 0.65).

An essential feature of the process is that the monoisopropylphenol content of the first step alkylation product is increased (in the distilland) by distillation. Increasing the monoisopropylphenol content is accomplished by distillation rather than increasing the degree of alkylation ($C_3/\phi$ ratio over 0.3) in the first process step. This two step method results in monoisopropylphenol/phenol feedstock with a $C_3/\phi$ ratio as high as desired with as low a level of polyisopropylphenols as desired. The polyisopropyl phenol content is reduced by conducting the first step alkylation to as low as $C_3/\phi$ ratio as required to eliminate or reduce polyisopropylphenol formation. Thereafter, the phenolic feedstock is prepared to as high a monoisopropylphenol content as desired by removing a proportion of unreacted phenol as distillate. The process sequence of (1) alkylation and (2) distillative fractionation is limited only by practical operating limits of how little monoisopropylphenol to form in the first step and/or how much phenol distillate to remove in the second step. If desired, the isopropyl phenol product of the two step alkylation/fractionation process may be mixed with other substituted or unsubstituted phenols to give a feedstock suitable for phosphorylation. However, it is the contemplated practice of this invention that all or at least a major part of the feedstock be formed by the two step alkylation/fractionation process of this invention.

Phosphorylation Step

The phosphorylation of the alkylated phenol product produced by the first and second steps of this invention may be carried out by any conventional phosphorylation procedure such as described in U.S. Pat. Nos. Re. 29,540, and 4,139,487 and 4,103,096 the disclosures of which are incorporated herein by reference. Conventional phosphorylating agents are phosphoric acid, phosphorus oxychloride, and phosphorus pentachloride. The proportion of phosphorylating agent to alkylated phenol and phenol may be varied over a wide range but is preferably within the range of one to five moles of phenol or alkylated phenol per mole of phosphorylating agent. The triaryl phosphates produced in accordance with the present invention have use as plasticizers for polymers such as polyvinylchloride. The phosphate esters of this invention may also be used as lubricants and hydraulic fluids. It is a particular advantage of the process of this invention that the phosphate ester products have reduced susceptibility to color formation. The following examples illustrate the invention.

EXAMPLE I

This example illustrates the alkylation of phenol with propylene and the consequent distribution of alkylation products.

Four portions of phenol were alkylated with propylene in the presence of 1% by weight p-toluene sulfonic acid catalyst. The isopropylation product was analyzed by gas chromatography. Experimental results are shown in Table I below:

TABLE I

| Sample No. | Initial Weight Phenol (grams) | $C_3/\phi$ Mole Ratio | Phenol* (Wt. %) | Total* Monoisopropyl phenol (Wt. %) | 2,6-Di-* isopropyl phenol (wt. %) | Total Di-* isopropyl phenol (wt. %) |
|---|---|---|---|---|---|---|
| 1 | 3575.1 | 0.141 | 78.7 | 16.2 | 0.67 | 1.6 |
| 2 | 3624.9 | 0.203 | 73.8 | 22.9 | 1.17 | 2.5 |
| 3 | 3515.9 | 0.247 | 68.7 | 25.9 | 1.77 | 3.8 |
| 4 | 3760.0 | 0.308 | 62.3 | 28.2 | 2.56 | 6.4 |

*Gas chromatographic analysis

EXAMPLE II

Phenol was alkylated in a 5 liter flask using a 1% concentration of p-toluene sulfonic acid catalyst. Gaseous propylene was sparged into the liquid phenol reaction medium in a manner to provide agitation. The propylene adsorption rate was $2.4 \times 10^{-4}$ gms propylene per grams of phenol per minute.

Two batches of phenol were isopropylated to $C_3/\phi$ levels of 0.15 and 0.20. Each alkylation product was distilled in a single plate distillation apparatus. Both the distillate and distilland were analyzed by gas chromatography during the course of the distillation. The results of this experiment are set out in Tables II and III below:

TABLE II

FRACTIONATION OF $C_3\phi \cong 0.15$ PHENOL ISOPROPYLATION REACTION MIXTURE

| | | | | DISTILLAND ANALYSIS WT. % | | | |
|---|---|---|---|---|---|---|---|
| Sample No. | Distillation temp °C. | Distilland Wt. Gms. | $C_3/\phi$ Mole Ratio | Phenol | Total Monoisopropyl phenol | 2,6-Di-isopropyl phenol | Total Diisopropyl phenol |
| Start | — | 3,682 | .141 | 78.7 | 16.2 | .67 | 1.6 |
| 5 | 186 | 3,436 | .163 | 78.9 | 19.4 | .87 | 1.7 |
| 6 | 186 | 3,260 | .177 | 77.2 | 21.0 | .90 | 1.8 |
| 7 | 186 | 3,050 | .181 | 76.8 | 21.3 | .95 | 1.9 |
| 8 | 186 | 2,803 | .194 | 75.1 | 22.9 | 1.04 | 2.0 |
| 9 | 187 | 2,507 | .256 | 68.1 | 28.9 | 1.23 | 2.8 |
| 10 | 187 | 2,259 | .270 | 67.0 | 28.7 | 1.43 | 3.9 |
| 11 | 187 | 2,024 | .250 | 69.1 | 27.9 | 1.42 | 3.1 |

TABLE II-continued

FRACTIONATION OF $C_3/\phi \cong 0.15$ PHENOL ISOPROPYLATION REACTION MIXTURE

| Sample No. | Distillation temp °C. | Distilland Wt. Gms. | $C_3/\phi$ Mole Ratio | DISTILLAND ANALYSIS WT. % |  |  |  |
|---|---|---|---|---|---|---|---|
| | | | | Phenol | Total Monoisopropyl phenol | 2,6-Di-isopropyl phenol | Total Diisopropyl phenol |
| 12 | 189 | 1,791 | .284 | 65.5 | 30.7 | 1.61 | 3.8 |
| 13 | 190 | 1,606 | .304 | 63.2 | 33.0 | 1.66 | 3.8 |
| 14 | 190 | 1,400 | .359 | 58.0 | 36.7 | 1.86 | 5.3 |
| 15 | 191 | 1,180 | .426 | 52.2 | 40.1 | 2.21 | 7.6 |
| 16 | 190 | 1,044 | .466 | 48.7 | 42.8 | 2.33 | 8.5 |
| 17 | 193 | 844 | .566 | 40.7 | 46.7 | 2.66 | 11.9 |
| 18 | 196 | 797 | .629 | 36.9 | 47.4 | 2.44 | 15.3 |

TABLE III

FRACTIONATION OF $C_3/\phi \cong 0.20$ PHENOL ISOPROPYLATION REACTION MIXTURE*

| Sample No. | Distillation temp °C. | Distilland Wt. Gms. | $C_3/\phi$ Mole Ratio | DISTILLAND ANALYSIS WT. %** |  |  |  |
|---|---|---|---|---|---|---|---|
| | | | | Phenol | Total Monoisopropyl phenol | 2,6-Di-isopropyl phenol | Total Diisopropyl phenol |
| Start | — | 3,938 | .204 | 70.5 | 22.9 | 1.36 | 2.7 |
| 19 | 186 | 3,714 | .235 | 70.9 | 25.8 | 1.59 | 3.3 |
| 20 | 187 | 3,521 | .240 | 70.4 | 26.0 | 1.74 | 3.5 |
| 21 | 187 | 3,331 | .249 | 69.6 | 26.6 | 1.74 | 3.8 |
| 22 | 187 | 3,145 | .271 | 67.0 | 29.0 | 1.94 | 3.9 |
| 23 | 188 | 2,924 | .283 | 65.8 | 30.2 | 1.99 | 4.0 |
| 24 | 188 | 2,711 | .290 | 65.1 | 30.7 | 1.89 | 4.2 |
| 25 | 189 | 2,420 | .320 | 62.1 | 32.8 | 2.24 | 5.1 |
| 26 | 190 | 2,309 | .354 | 59.1 | 34.5 | 2.16 | 6.4 |
| 27 | 191 | 2,105 | .374 | 57.1 | 36.3 | 2.68 | 6.6 |
| 28 | 191 | 1,958 | .404 | 54.4 | 38.1 | 3.16 | 7.5 |
| 29 | 193 | 1,759 | .449 | 50.6 | 40.4 | 2.67 | 8.9 |
| 30 | 194 | 1,573 | .499 | 46.6 | 42.7 | 3.32 | 10.7 |
| 31 | 195 | 1,363 | .560 | 41.0 | 48.0 | 3.54 | 11.0 |
| 32 | 195 | 1,291 | .604 | 37.4 | 50.2 | 3.66 | 11.9 |

*Prepared by a method such as described in Example 1
**Wt. % based on gas chromatographic analysis The data in the Tables II and III show that the 0.15 $C_3/\phi$ alkylation product has a significantly lower 2,6-diisopropylphenol content than the 0.20 $C_3/\phi$ alkylation product when both products are compared as distillands at the same alkylation level ($C_3/\phi=0.5$) resulting from a simple single plate distillation.

The process of this invention may be performed by operating according to the following steps:

Phenol is alkylated with propylene in the presence of 1% by weight (based on phenol) of p-toluene sulfonic acid catalyst. The alkylation is conducted until the ratio of the moles of propylene reacted with the total moles of phenol is about 0.20. The alkylation product is distilled to yield a distilland having a propylene (reacted) to phenol mole ratio of 0.5. The distilland is then phosphorylated using POCl₃ in a conventional manner to yield an isopropylphenyl/phenyl phosphate having a reduced 2,6-diisopropylphenyl/phenyl phosphate content.

What is claimed is:

1. A process for preparing monoisopropylphenyl/phenyl phosphate containing mixtures by isopropylating phenol and phosphorylating the isopropylation product; wherein the improvement comprises the sequential steps of:
   (A) alkylating phenol with propylene using a p-toluene sulfonic acid catalyst under conditions effective to yield an isopropylated product having a $C_3/\phi$ ratio of less than 0.25;
   (B) distilling the isopropylated product of step (A) to remove unreacted phenol to yield a fractionated product having a $C_3/\phi$ ratio of at least 0.30;
   (C) phosphorylating the distilled product of step (B) to yield a monoisopropylphenyl/diphenyl phosphate containing mixture having a reduced 2,6-diisopropylphenyl/phenyl phosphate content.

2. The process of claim 1 wherein the isopropylation of step (A) is conducted to yield a $C_3/\phi$ ratio of from 0.05 to 0.20.

3. The process of claim 1 wherein the fractionation of step (B) is conducted to yield a $C_3/\phi$ ratio of from 0.35 to 0.65.

4. The process of claim 1 wherein the catalyst concentration is from 0.05 to 10.0 weight percent based on the weight of phenol.

5. The process of claim 1 wherein the phosphorylating agent used in step (C) is POCl₃.

* * * * *